(12) United States Patent
Fenouil et al.

(10) Patent No.: US 7,087,777 B2
(45) Date of Patent: Aug. 8, 2006

(54) PROCESS FOR PREPARING A BRANCHED OLEFIN, A METHOD OF USING THE BRANCHED OLEFIN FOR MAKING A SURFACTANT, AND A SURFACTANT

(75) Inventors: Laurent Alain Michel Fenouil, Twickenham (GB); Brendan Dermot Murray, Houston, TX (US); Paul Marie Ayoub, Houston, TX (US)

(73) Assignee: Shell Oil Company, Houston, TX (US)

( * ) Notice: Subject to any disclaimer, the term of this patent is extended or adjusted under 35 U.S.C. 154(b) by 172 days.

(21) Appl. No.: 10/738,572

(22) Filed: Dec. 17, 2003

(65) Prior Publication Data

US 2004/0133037 A1    Jul. 8, 2004

Related U.S. Application Data

(62) Division of application No. 10/075,682, filed on Feb. 14, 2002, now Pat. No. 6,765,106.

(60) Provisional application No. 60/269,874, filed on Feb. 15, 2001.

(51) Int. Cl.
    *C07C 303/24*    (2006.01)
(52) U.S. Cl. .................... 558/41; 510/155; 585/513
(58) Field of Classification Search .................. 558/41; 510/155; 585/513
    See application file for complete search history.

(56) References Cited

U.S. PATENT DOCUMENTS

| | | | |
|---|---|---|---|
| 3,231,621 A | 1/1966 | Slaugh | 260/604 |
| 3,239,566 A | 3/1966 | Slaugh et al. | 260/604 |
| 3,239,569 A | 3/1966 | Slaugh et al. | 260/632 |
| 3,239,570 A | 3/1966 | Slaugh et al. | 260/632 |
| 3,239,571 A | 3/1966 | Slaugh et al. | 260/632 |
| 3,253,055 A | 5/1966 | Goble et al. | 260/683.75 |
| 3,274,287 A | 9/1966 | Moore et al. | 260/683.3 |
| 3,315,007 A | 4/1967 | Abell, Jr. et al. | 260/683.3 |
| 3,315,008 A | 4/1967 | Abell, Jr. et al. | 260/683.3 |
| 3,420,875 A | 1/1969 | Di Salvo et al. | 260/513 |
| 3,420,898 A | 1/1969 | Van Winkle et al. | 260/632 |
| 3,427,342 A | 2/1969 | Brooks et al. | 260/458 |
| 3,428,654 A | 2/1969 | Rubinfeld et al. | 260/327 |
| 3,440,291 A | 4/1969 | Van Winkle | 260/632 |
| 3,448,157 A | 6/1969 | Slaugh | 260/604 |
| 3,448,158 A | 6/1969 | Slaugh et al. | 260/604 |
| 3,462,525 A | 8/1969 | Levinsky et al. | 424/56 |
| 3,496,203 A | 2/1970 | Morris et al. | 260/439 |
| 3,496,204 A | 2/1970 | Morris et al. | 260/439 |
| 3,501,515 A | 3/1970 | Van Winkle | 260/439 |
| 3,506,580 A | 4/1970 | Rubinfeld et al. | 252/138 |
| 3,524,864 A | 8/1970 | Rubinfeld et al. | 260/327 |
| 3,527,818 A | 9/1970 | Mason et al. | 260/632 |
| 3,562,797 A | 2/1971 | Hu | 260/683.3 |
| 3,579,537 A | 5/1971 | Rubinfeld | 260/327 |
| 3,709,817 A | 1/1973 | Suggiti et al. | 208/112 |
| 3,711,399 A | 1/1973 | Estes et al. | 208/112 |
| 3,745,112 A | 7/1973 | Rausch | 208/139 |
| 3,755,146 A | 8/1973 | Harris et al. | 208/112 |
| 4,430,517 A | 2/1984 | Imai et al. | 585/660 |
| 5,012,021 A | 4/1991 | Vora et al. | 585/315 |
| 5,112,519 A | 5/1992 | Giacobbe et al. | 252/174.21 |
| 5,218,086 A | 6/1993 | Van Doorn et al. | 528/392 |
| 5,292,983 A | 3/1994 | Sie | 585/733 |
| 5,510,306 A | 4/1996 | Murray | 502/64 |
| 5,833,839 A | 11/1998 | Wittenbrink et al. | 208/112 |
| 5,849,960 A * | 12/1998 | Singleton et al. | 568/909 |
| 5,866,748 A | 2/1999 | Wittenbrink et al. | 585/734 |
| 5,906,727 A | 5/1999 | Wittenbrink et al. | 208/14 |
| 5,948,719 A | 9/1999 | Johnson et al. | 502/73 |
| 6,013,171 A | 1/2000 | Cook et al. | 208/27 |
| 6,037,506 A | 3/2000 | Bolinger | 568/909 |
| 6,111,158 A | 8/2000 | Marinangeli et al. | 585/467 |
| 6,566,565 B1 | 5/2003 | Murray et al. | 568/909 |

FOREIGN PATENT DOCUMENTS

| | | |
|---|---|---|
| EP | 0 654 521 A1 | 11/1994 |
| EP | 0903333 B1 | 11/2001 |
| WO | WO 97/01521 | 1/1997 |
| WO | WO 99/05082 | 2/1999 |
| WO | WO 99/05084 | 2/1999 |
| WO | WO 99/5244 | 2/1999 |
| WO | WO 99/54277 | 10/1999 |
| WO | 02/064707 A2 | 8/2002 |

OTHER PUBLICATIONS

PCT Written Opinion for TH1837 PCT—International Patent Application No. PCT/EP02/01700.
"Microbial Polysaccharides" and "Molecular Sieves." *Kirk-Othmer Encyclopedia of Chemical Technology*, 4th Edition, vol. 1, pp. 589-591 and vol. 16, pp. 911-916.

(Continued)

*Primary Examiner*—Kamal A. Saeed

(57) ABSTRACT

A process for preparing branched olefins comprising 0.5% or less quaternary aliphatic carbon atoms, which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches, and which isoparaffinic composition may be obtained by hydrocracking and hydroisomerization of a paraffinic wax; a method of using olefins for making an anionic surfactant, a nonionic surfactant or a cationic surfactant, in particular a surfactant sulfate or sulfonate, comprising converting the branched olefins into the surfactant; and an anionic surfactant, a nonionic surfactant or a cationic surfactant which is obtainable by the method of use.

12 Claims, No Drawings

OTHER PUBLICATIONS

"UOP Molex Process for Production of Normal Paraffins," by Stephen W. Sohn, *Handbook of Petroleum Refining Processes*, (R. A. Meyers, Ed.) 2nd Edition, pp. 10.45-10.51, 10.75-10.81.

Monohydric Alcohols: Manufacture, Applications and Chemistry, E. J. Wickson (Ed.), Am. Chem. Soc. 1981, pp. 159-164.

U.S. Appl. No. 10/075,318, filed Feb. 14, 2002, Fenouil et al.

U.S. Appl. No. 60/511,211, filed Oct. 15, 2003, Ayoub et al.

International Search Report for PCT/EP 02/01700 of Oct. 4, 2002.

\* cited by examiner

PROCESS FOR PREPARING A BRANCHED OLEFIN, A METHOD OF USING THE BRANCHED OLEFIN FOR MAKING A SURFACTANT, AND A SURFACTANT

This is a division of application Ser. No. 10/075,682 filed Feb. 14, 2002 now U.S. Pat. No. 6,765,106, the entire disclosure of which is hereby incorporated by reference, which claims the benefit of U.S. Provisional Application No. 60/269,874 filed Feb. 15, 2001, the entire disclosure of which is hereby incorporated by reference.

FIELD OF THE INVENTION

This invention relates to a process for preparing a branched olefin, to a method of using the branched olefin for making a surfactant, and to the surfactant per se.

BACKGROUND OF THE INVENTION

U.S. Pat. No. 5,849,960 relates to surfactant sulfates based on branched alcohols. The branched alcohols in question have an average number of branches per molecule chain of at least 0.7. The branching comprises not only methyl branching but also ethyl branches, whilst the occurrence of longer branching is not excluded. The branched alcohols are made from branched olefins, which are made by skeletally isomerizing linear olefins. The surfactant sulfates of U.S. Pat. No. 5,849,960 simultaneously satisfy requirements for biodegradability, cold water solubility and cold water detergency.

The market always asks for improvements in the performance of existing detergent formulations, inter alia by improving the surfactants present in the detergent formulations. For example, the laundry market asks for improvements in the surfactants=biodegradability, their cold water solubility and their cold water detergency. At least an improvement is sought in the balance of the properties. By the terminology "an improvement in the balance of the properties" it is meant that at least one property is improved, whilst at least one of the other properties is not deteriorated.

The present invention seeks to provide improvements in the performance of the surfactant sulfates of U.S. Pat. No. 5,849,960, or at least in an improvement in the balance of their performance properties. Relevant performance properties are biodegradability, cold water solubility and cold water detergency, for example cold water detergency in water of low hardness and in water of high hardness. Other relevant performance properties are the compatibility of the surfactant sulfates with other components present in detergent formulations, as described hereinafter, in particular, the compatibility with enzymes, i.e. the inability of the surfactant sulfates to denature enzymes during storage in an aqueous medium. Again other relevant performance properties, in particular for personal care applications, are mildness to the skin and to the eyes and the ability of high foaming, preferably providing foam with a fine structure of the foam cells. Further, an improved performance is sought as a chemical for enhanced oil recovery applications and for the removal of oil spillage, viz. an improved ability to emulsify oil/water. and oil/brine systems and to stabilize emulsions of oil and water or brine, in particular at high temperature. Independently, the present invention seeks to provide a method for the manufacture of surfactant sulfates which is more versatile and economically more attractive than the method known from U.S. Pat. No. 5,849,960. In analogy, the invention seeks to provide similar improvements with respect to anionic surfactants, non-ionic surfactants and cationic surfactants, other than the surfactant sulfates mentioned hereinbefore, and their methods of manufacture.

SUMMARY OF THE INVENTION

In accordance with this invention surfactant sulfates are prepared by dehydrogenating selected branched paraffins to produce branched olefins. These branched olefins can be converted into branched alcohols and subsequently into surfactant sulfates. Alternatively, the branched olefins can be converted into other surfactant types, in particular anionic surfactants other than the surfactant sulfates, such as surfactant sulfonates; nonionic surfactants and cationic surfactants. It is an advantage of this invention that surfactants and intermediates can be made with a very low content of molecules, which have a linear carbon chain. It is another advantage of the invention that products can be made of which the molecules have a low content of branches having three or more carbon atoms. It is also an advantage of the invention that products can be made of which the molecules have a low content of quaternary aliphatic carbon atoms. Without wishing to be bound by theory, it is believed that the presence of quaternary aliphatic carbon atoms in the molecules of the surfactants prevents to some extent their biodegradation and the presence of quaternary aliphatic carbon atoms in the isoparaffinic composition is therefore preferably avoided. In fact, it has been determined that the presence of 0.5% or less quaternary aliphatic carbon atoms in the molecules of the surfactants renders the surfactants substantially more biodegradable.

Accordingly, the present invention provides a process for preparing branched olefins which process comprises dehydrogenating an isoparaffinic composition over a suitable catalyst which isoparaffinic composition comprises paraffins having a carbon number in the range of from 7 to 35, of which paraffins at least a portion of the molecules is branched, the average number of branches per paraffin molecule being at least 0.7 and the branching comprising methyl and optionally ethyl branches.

The invention also provides a method of using olefins for making an anionic surfactant, a nonionic surfactant or a cationic surfactant, in particular a surfactant sulfate or sulfonate, comprising converting branched olefins into the surfactant which branched olefins have been obtained in accordance with this invention.

Further, the invention provides a process for preparing alcohol sulfates, comprising converting branched olefins into branched alcohol sulfates which branched olefins have been obtained in accordance with this invention.

In a further aspect the present invention provides a branched olefin composition comprising olefins having different, consecutive carbon numbers in the range of from 7 to 35, of which olefins at least a portion of the molecules is branched, the average number of branches per molecule being at least 0.7 and the branching comprising methyl and optionally ethyl branches.

In again a further aspect the present invention provides a branched alcohol composition which is obtainable by a process comprising reacting branched olefins according to this invention with carbon monoxide and hydrogen.

In again a further aspect the present invention provides an anionic surfactant, a nonionic surfactant and a cationic surfactant, in particular a surfactant sulfate or sulfonate, which is obtainable by a method of use in accordance with this invention.

In again a further aspect the present invention provides an isoparaffinic composition comprising paraffins having different, consecutive carbon numbers in the range of from 7 to 35, of which paraffins at least a portion of the molecules is branched, the average number of branches per paraffin molecule being at least 1.5 and the branching comprising methyl and optionally ethyl branches.

In again a further aspect the invention provides a branched olefin composition which is obtainable in accordance with this invention.

Without wishing to be bound by theory, it is believed that any improvement in the performance properties of the surfactant sulfates prepared in accordance with this invention, compared with the surfactant sulfates specifically known from U.S. Pat. No. 5,849,960, resides in a difference in the distribution of branching along the respective paraffinic chains. Such differences in the distribution of branching are truly unexpected in view of the prior art and, therefore, they are inventive.

DETAILED DESCRIPTION OF THE INVENTION

As described herein, the isoparaffinic composition and the compositions of branched olefins and alcohols derived therefrom are generally mixtures comprising molecules with different, consecutive carbon numbers. Typically at least 75% w, more typically at least 90% w, of these compositions represent a range of molecules of which the heaviest molecules comprises at most 6 carbon atoms more than the lightest molecules.

The isoparaffinic composition comprises paraffins having a carbon number in the range of from 7 to 35, of which paraffins at least a portion of the molecules is branched. Preferably, the isoparaffinic composition comprises paraffins having a carbon number in the range of from 10 to 18. Preferably at least 75% w, more preferably at least 90% w, of the isoparaffinic composition consists of paraffins having a carbon number in the range of from 10 to 18. In practice, frequently at most 99.99% w, more frequently at most 99.9% w, of the isoparaffinic composition consists of paraffins having a carbon number in the range of from 10 to 18. When it is intended to prepare surfactant sulfates from the isoparaffinic composition it is preferred that the isoparaffinic composition comprises paraffins having a carbon number in the range of from 14 to 17, in which case preferably at least 75% w, more preferably at least 90% w, of the isoparaffinic composition consists of paraffins having a carbon number in the range of from 14 to 17. In practice, frequently at most 99.99% w, more frequently at most 99.9% w, of the isoparaffinic composition consists of paraffins having a carbon number in the range of from 14 to 17. These selections are based on the effects that the paraffins of a lower carbon number ultimately yield surfactants which are more volatile and that the paraffins of a higher carbon number ultimately yield surfactants with less water solubility.

The average number of branches per paraffin molecule present in the isoparaffinic composition is at least 0.7, calculated over the total of the branched paraffins and, if present, the linear paraffins. Suitably the average number of branches is at least 0.8, and preferably at least 0.9, for example 1.0. Suitably the average number of branches is at most 2.0, preferably at most 1.5, and in particular at most 1.4. On the other hand, for some applications it may be desirable that the average number of branches is at least 1.5 and suitably at most 2.5.

The number of methyl branches present in the isoparaffinic composition is suitably at least 20%, more suitably at least 40%, preferably at least 50% of the total number of branches. In practice the number of methyl branches is frequently at most 99%, more frequently at most 98% of the total number of branches. If present, the number of ethyl branches is suitably at least 0.1%, in particular at least 1%, more in particular at least 2% of the total number of branches. Suitably, the number of ethyl branches is at most 20%, in particular at most 15%, more in particular at most 10% of the total number of branches. The number of any branches, if present, other than methyl and ethyl branches, may be less than 10%, in particular less than 5% of the total number of branches. The number of any branches, if present, other than methyl and ethyl branches, may be more than 0.1%, typically more than 1% of the total number of branches.

The number of quaternary aliphatic carbon atoms present in the isoparaffinic composition is preferably low. For applications where biodegradability is not as critical, the number of quaternary aliphatic carbon atoms is suitably less than 2% of the carbon atoms present, more suitably less than 1%. For any application, and particularly for applications where biodegradability is important, the number of quaternary aliphatic carbon atoms preferably is 0.5% or less, most preferably less than 0.5%, and in particular less than 0.3%. In practice the number of quaternary aliphatic carbon atoms present in the isoparaffinic composition is frequently more than 0.01% of the aliphatic carbon atoms present, more frequently more than 0.05%.

The content of branched paraffins of the isoparaffinic composition is typically at least 70% w, more typically at least 90% w, preferably at least 95% w, more preferably at least 99% w, in particular at least 99.9% w, relative to the weight of the isoparaffinic composition. In practice the content of branched paraffins is frequently at most 99.99% w, more frequently at most 99.95% w, relative to the weight of the isoparaffinic composition. The content of linear paraffins of the isoparaffinic composition is typically at most 30% w, more typically at most 10% w, preferably at most 5% w, more preferably at most 1% w, in particular at most 0.1% w, relative to the weight of the isoparaffinic composition. In practice the content of linear paraffins is frequently at least 0.01% w, more frequently at least 0.05% w, relative to the weight of the isoparaffinic composition.

The isoparaffinic composition may originate from various sources. For example, suitable isoparaffinic compositions may be selected from crude oil distillation fractions. Such crude oil distillation fractions may be treated to partially or, more preferably, completely remove sulfur and/or nitrogen containing components.

Alternately, the isoparaffinic composition may be obtained by hydroisomerization of a paraffinic composition, i.e. a composition which comprises predominantly linear paraffins, such as obtainable from a Fischer Tropsch process or from an ethylene oligomerization process. Linear paraffins obtained in a Fischer Tropsch synthesis are particularly preferred because Fischer Tropsch products are generally very low in their content of sulfur and nitrogen and they are cost effective. The Fischer Tropsch products may or may not comprise oxygenates. The product obtained in the hydroisomerization process may be fractionated, for example, by distillation or otherwise, in order to isolate an isoparaffinic product of the desired composition. Such a hydroisomerization process and subsequent fractionation is known, for example from U.S. Pat. No. 5,866,748, which is incorporated herein by reference.

Preferably, the isoparaffinic composition is obtained by hydrocracking and hydroisomerization of a paraffinic wax, in particular a slack wax, a wax obtained in a Fischer Tropsch synthesis or a polyethylene wax. The paraffinic wax comprises typically linear paraffins having at least 5 carbon atoms, preferably at least 15 carbon atoms, more preferably at least 25 carbon atoms. In practice, the paraffinic wax comprises frequently linear paraffins of which the number of carbon atoms may be high, for example up to 100 or up to 200 and even more. Wax obtained in a Fischer Tropsch synthesis is particularly preferred because these are generally very low in their content of sulfur and nitrogen and they are cost effective. The product obtained in the hydrocracking/hydroisomerization process may be fractionated, for example, by distillation or otherwise, in order to isolate an isoparaffinic product of the desired composition. Such a hydrocracking/hydro-isomerization process and subsequent fractionation is known, for example from U.S. Pat. No. 5,833,839, which is incorporated herein by reference. Generally, the hydrocracking/hydroisomerization process involves hydrocracking with simultaneous hydroisomerization.

The isoparaffinic composition may be treated to lower the content of linear paraffins, in order to favorably adjust the average number of branches in the isoparaffinic composition. Such separation may be accomplished by separation using a molecular sieve as absorbent. The molecular sieve may be, for example, a zeolite 4A, a zeolite 5A, a zeolite X or a zeolite Y. Reference may be made to AKirk-Othmer Encyclopedia of Chemical Technology@, 4$^{th}$ edition, Volume 1, pp. 589–590, and Volume 16, pp. 911–916; and A Handbook of Petroleum Refining Processes@ (R A Meyers, Ed.), 2$^{nd}$ edition, pp. 10.45–10.51, 10.75–10.77. These references are incorporated herein by reference.

Catalysts suitable for the dehydrogenation of the isoparaffinic composition may be selected from a wide range. For example, they may be based on a metal or metal compound deposited on a porous support, the metal or metal compound being one or more selected for example from chrome oxide, iron oxide and, preferably, the noble metals. The noble metals are understood to be the metals of the group formed by platinum, palladium, iridium, ruthenium, osmium and rhodium. Preferred noble metals are palladium and, in particular platinum.

Suitable porous supports may be supports of a carbon nature such as activated carbon, coke and charcoal; silica or silica gel, or other natural or synthetic clays or silicates, for example hydrotalcites; ceramics; refractory inorganic oxides such as alumina, titania or magnesia; naturally or synthetic crystalline alumino-silicates such as mordenite or faujasite; and combinations of two or more elements selected from these groups. The porous support is preferably an alumina, in particular gamma alumina or eta alumina.

The quantity of the metal or metal compound deposited on the porous support is not material to this invention. The quantity may suitably be selected in the range of from 0.01 to 5% w, preferably from 0.02 to 2% w, based on the weight of the catalyst.

Further metals may be present in the catalyst used for the dehydrogenation of the isoparaffinic composition, in particular in the catalysts which comprise a noble metal. Such further metals may suitably be selected from Group 3a, Group 4a and Group 5a of the Periodic Table of Elements (cf. R C Weast (Ed,) A Handbook of Chemistry and Physics@, 54$^{th}$ edition, CRC Press, inside cover). In particular, indium may be selected from Group 3a, tin may be selected from Group 4a or bismuth may be selected from Group 5a. Especially suitable further metals are alkali and alkaline earth metals. Preferred alkali metals are potassium, and in particular lithium.

Further elements, which may be present in the catalyst used for the dehydrogenation of the isoparaffinic composition, are halogens, in particular in combination with a metal of Group 4a, more in particular in combination with tin. Chlorine is a preferred halogen.

The quantity of such further metals or halogens may independently be in the range of from 0.01 to 5% w, preferably from 0.02 to 2% w, based on the weight of the catalyst.

Suitable catalysts for the dehydrogenation of the isoparaffinic composition are, for example, chrome oxide on gamma alumina, platinum on gamma alumina, palladium on gamma alumina, platinum/lithium on gamma alumina, platinum/potassium on gamma alumina, platinum/tin on gamma alumina, platinum/tin on hydrotalcite, platinum/indium on gamma alumina and platinum/bismuth on gamma alumina.

The dehydrogenation may be operated at a wide range of conditions. Suitably the temperature is in the range of from 300° C. to 700° C., more suitably in the range of from 400° C. to 600° C., in particular in the range of from 450 to 550° C. The total pressure may be an elevated pressure, such as in the range of from 1.1 to 15 bara (i.e. bar absolute), preferably in the range of from 1.3 to 10 bara, in particular in the range of from 1.5 to 5 bara. In order to prevent coking, hydrogen may be fed together with the isoparaffinic composition. Suitably, hydrogen and paraffins present in the isoparaffinic composition are fed at a molar ratio in the range of from 0.1 to 20, more suitably this molar ratio is in the range of from 0.5 to 15, in particular this molar ratio is in the range of from 1 to 10.

The residence time in the dehydrogenation is typically selected such that conversion level of the isoparaffinic composition is kept below 50 mole-%, preferably in the range of from 5 to 30 mole-%, in particular in the range of from 10 to 20 mole-%. By keeping the conversion level low, side reactions may to some extent be prevented, such as diene formation and cyclization reactions. Non-converted paraffins and dehydrogenated compounds may be separated from the dehydrogenation product and, if desired, non-converted paraffins may be recycled to the dehydrogenation step. Such separation may be accomplished by extraction, by extractive distillation or, preferably, by using a molecular sieve as absorbent. The molecular sieve may be, for example, a zeolite 4A, a zeolite 5A, a zeolite X or a zeolite Y. If desired, linear olefins may be separated at least to some extent from branched olefin so that the content of branched olefin in the product as obtained from the dehydrogenation is increased further, but this option is generally not preferred.

The skilled person is aware of the techniques of preparing the catalysts, performing the dehydrogenation step and performing associated separation steps, for use in this invention. For example, suitable procedures for preparing catalysts and performing the dehydrogenation are known from U.S. Pat. Nos. 5,012,021, 3,274,287, 3,315,007, 3,315,008, 3,745,112, 4,430,517, incorporated herein by reference. For techniques suitable for the separation of branched olefins from linear olefins, reference may be made to AKirk-Othmer Encyclopedia of Chemical Technology@, 4$^{th}$ edition, Volume 1, pp. 589–591, and Volume 16, pp. 911–916; and A Handbook of Petroleum Refining Processes@ (R A Meyers, Ed.), 2$^{nd}$ edition, pp. 10.45–10.51, 10.79–10.81. These references are incorporated herein by reference.

The dehydrogenation in accordance with this invention yields typically a branched olefin composition comprising olefins having a carbon number in the range of from 7 to 35, of which olefins at least a portion of the molecules is branched, the average number of branches per molecule being at least 0.7 and the branching comprising methyl and optionally ethyl branches. Preferably, the branched olefin composition comprises olefins having a carbon number in the range of from 10 to 18. Preferably at least 75% w, more preferably at least 90% w, of the branched olefin composition consists of olefins having a carbon number in the range of from 10 to 18. In practice, frequently at most 99.99% w, more frequently at most 99.9% w, of the branched olefin composition consists of olefins having a carbon number in the range of from 10 to 18. When it is intended to prepare surfactant sulfates from the branched olefin composition it is preferred that the branched olefin composition comprises olefins having a carbon number in the range of from 14 to 17, in which case preferably at least 75% w, more preferably at least 90% w, of the branched olefin composition consists of olefins having a carbon number in the range of from 14 to 17. In practice, frequently at most 99.99% w, more frequently at most 99.9% w, of the branched olefin composition consists of olefins having a carbon number in the range of from 14 to 17.

Suitably the average number of branches per olefin molecule present in the branched olefin composition is at least 0.8, and preferably at least 0.9, for example 1.0. Suitably the average number of branches is at most 2.0, preferably at most 1.5, and in particular at most 1.4. The number of methyl branches is suitably at least 20%, more suitably at least 40%, preferably at least 50% of the total number of branches. In practice the number of methyl branches is frequently at most 99%, more frequently at most 98% of the total number of branches. If present, the number of ethyl branches is suitably at least 0.1%, in particular at least 1%, more in particular at least 2% of the total number of branches. Suitably, the number of ethyl branches is at most 20%, in particular at most 15%, more in particular at most 10% of the total number of branches. The number of any branches, if present, other than methyl and ethyl branches, may be less than 10%, in particular less than 5% of the total number of branches. The number of any branches, if present, other than methyl and ethyl branches, may be more than 0.1%, typically more than 1% of the total number of branches.

The number of quaternary aliphatic carbon atoms present in the branched olefins is preferably low. For applications where biodegradability is not as critical, the number of quaternary aliphatic carbon atoms is suitably less than 2% of the carbon atoms present, more suitably less than 1%. For any application, and particularly for applications where biodegradability is important, the number of quaternary aliphatic carbon atoms preferably is 0.5% or less, most preferably less than 0.5%, and in particular less than 0.3%. In practice the number of quaternary aliphatic carbon atoms present in the branched olefins is frequently more than 0.01% of the aliphatic carbon atoms present, more frequently more than 0.05%.

The content of branched olefins of the branched olefin composition is typically at least 70% w, more typically at least 90% w, preferably at least 95% w, more preferably at least 99% w, in particular at least 99.9% w, relatively to the weight of the branched olefin composition. In practice the content of branched olefins is frequently at most 99.99% w, more frequently at most 99.95% w, relatively to the weight of the branched olefin composition. The content of linear olefins of the branched olefin composition is typically at most 30% w, more typically at most 10% w, preferably at most 5% w, more preferably at most 1% w, in particular at most 0.1% w, relatively to the weight of the branched olefin composition. In practice the content of linear olefins is frequently at least 0.01% w, more frequently at least 0.05% w, relative to the weight of the branched olefins composition.

The branched olefin composition is suitable for the manufacture of anionic, nonionic, and cationic surfactants, preferably the former two, more preferably the anionic surfactants.

More preferably, the branched olefin composition is used for the manufacture of surfactant sulfates, including alcohol sulfates and oxyalkylated alcohol sulfates, or nonionic oxyalkylated alcohols. To this end, the branched olefins may be converted into branched alcohols. Preferably, the branched alcohols are branched primary alcohols. As an alternative, the branched alcohols may be branched secondary alcohols.

Conversion of the branched olefins into branched alcohols is conveniently accomplished, for example, by hydroformylation, by oxidation and hydrolysis, by sulfation and hydration, by epoxidations and hydration, or the like.

In hydroformylation, the branched olefins are converted into primary branched alcohols by reaction with carbon monoxide and hydrogen in the presence of a suitable catalyst. Methods of hydroformylation which are suitable for use in this invention are known from, for example, U.S. Pat. Nos. 3,231,621, 3,239,566, 3,239,569, 3,239,570, 3,239,571, 3,420,898, 3,440,291, 3,448,158, 3,448,157, 3,496,203, 3,496,204, 3,501,515, 3,527,818 and 6,037,506, the disclosures of which are incorporated herein by reference. Further methods are described in Kirk Othmer, A Encyclopedia of Chemical Technology@ $3^{rd}$ edition. Vol. 16, pages 637–653; A Monohydric Alcohols: Manufacture, Applications and Chemistry@, E J Wickson (Ed.), Am. Chem. Soc. 1981, incorporated herein by reference.

Hydroformylation is a term used in the art to denote the reaction of an olefin with carbon monoxide and hydrogen to produce an aldehyde or alcohol, which has one more carbon atom then the reactant olefin. Frequently, in the art, the term hydroformylation is utilized to cover the aldehyde and the reduction to the alcohol step in total, i.e., hydroformylation refers to the production of alcohols from olefins via carbonylation and an aldehyde reduction process. As used herein, hydro-formylation refers to the ultimate production of alcohols.

Suitable catalysts are based on a metal of Group 8 of the Periodic Table. Preferred metals of Group 8 may be selected from palladium, platinum, rhodium, nickel and cobalt, in particular from cobalt, rhodium and palladium. The Group 8 metal may or may not be used in the form of a complex compound in which the Group 8 is combined with a ligand, for example a phosphine, phosphite, arsine, stibine or pyridine ligand. Illustrative hydroformylation catalysts include cobalt hydrocarbonyl catalyst, cobalt-phosphine ligand catalyst, and rhodium-phosphine ligand catalyst.

The source of the Group 8 metal may be a salt. Preferred are salts of acids which have a pKa value of less than 6, in particular less than 4, more in particular less than 2, when measured in water at 20° C. Examples of suitable acids are nitric acid, sulfuric acid, carboxylic acids and sulfonic acids. Preferred carboxylic acids are the ∀-halocarboxylic acids, such as dichloroacetic acid, trifluoroactetic acid and perfluoropropionic acid. Preferred sulfonic acids are p-toluenesulfonic acid, benzenesulfonic acid and methanesulfonic acid.

It is also possible to employ as a source of the Group 8 metal the metallic element itself or a zero valence metal complex, for example a complex with carbon monoxide. This would require, however, the additional presence of a protic acid.

With respect to the ligands, mention may be made of monophosphines which comprise three hydrocarbyl and/or hydrocarbyloxy groups attached to phosphorus, and the corresponding arsines and stibines. Examples of the monophosphines are triamylphosphine, trihexylphosphine, dimethylethylphosphine, diamylethylphosphine, tricyclopentylphosphine, tricyclohexylphosphine, diphenylbutylphosphine, diphenylbenzylphosphine, diphenyl(2-pyridyl)phosphine, phenyl[bis(2-pyridyl)]phosphine, triethoxyphosphine, butyldiethoxyphosphine, triphenylphosphine, dimethylphenylphosphine, methyldiphenylphosphine, dimethylpropylphosphine, and the tritolylphosphines.

Alternatively, bidentate ligands may be used such as tetrahydrocarbylbisphosphines or the corresponding arsines or stibines. Examples of tetrahydrocarbyl-bisphosphines are 1,2-bis(dimethylphosphino)ethane, 1,2- and 1,3-bis(dimethylphosphino)propane, 1,2-bis(diethyl-phosphino) ethane, 1,2-bis[di(1-butyl)phosphino]ethane, 1-dimethylphosphino-2-diethylphosphinoethane, 1,2-bis(diphenylphosphino) ethane, 1,2-bis(diperfluorophenylphosphino)ethane, 1,3-bis(-diphenylphosphino)propane, 1,4-bis(diphenylphosphino) butane, 1-dimethylphosphino-2-diphenylphosphinoethane, 1-diethylphosphino-3-diphenylphosphinopropane and 1,2-bis[di(o-tolyl)phosphino]ethane.

Other suitable ligands are the phosphabicyclohydrocarbons, such as 9-hydrocarbyl-9-phospha-bicyclononane and P,P=-bis(9-phosphabicyclononyl)-hydrocarbons in which the smallest P-containing-ring contains at least 5 carbon atoms. Such ligands include 9-aryl-9-phosphabicyclo[4.2.1] nonanes, 9-(dialkylaryl)-9-phosphabicyclo[4.2.1]nonanes, 9-alkyl-9-phospha-bi.cyclo[4.2.1]nonanes, 9-cycloalkyl-9-phospha-bicyclo[4.2.1]nonanes, 9-cycloalkenyl-9-phosphabicyclo[4.2.1]nonanes, P,P=-bis(9-phosphabicyclononyl)alkanes and their [3.3.1] isomers. Specific examples of such ligands are 9-phenyl-9-phosphabicyclo [4.2.1]nonane, 9-(2,4-dimethylphenyl)-9-phosphabicyclo [4.2.1]nonane, 9-ethyl-9-phosphabicyclo [4.2.1]nonane, 9-cyclohexyl-9-phosphabicyclo[4.2.1]nonane, 9-cyclopentenyl-9-phospha-bicyclo[4.2.1]nonane, 1,2-P,P=-bis(9-phosphabicyclo-[4.2.1]nonyl)ethane, 1,3-P,P=-bis(9-phosspabicycl o-[4.2.1]nonyl)propane, 1,4-P, P=-bis(9-phosphabicyclo-[4.2.1]nonyl)butane and their [3.3.1] isomers.

The reaction conditions of the hydroformylation may be selected form wide ranges. For example, temperatures may be from 20° C. to 300° C. Temperatures in the range of from 150° C. to 250° C., in particular from 125 to 200° C., are generally recommended. Reaction pressures in the range of from 10 to 200 bara are typical, but lower or higher pressures may be selected. Reaction pressures in the range of from 20 to 100 bara are preferred. Molar ratios of catalyst to olefin ranging from 1:1000 to 1:1 are suitable. The ratio of hydrogen to carbon monoxide may be selected from wide ranges, but is usually above 1 to favor the formation of alcohol product. Preferably this molar ratio is in the range of from 2 to 10.

The hydroformylation process may or may not be carried out in the presence of an inert solvent. A variety of solvents may be applied, for example ketones such as acetone, methyl ethyl ketone, methyl isobutyl ketone, acetophenone and cyclohexanone; aromatic compounds such as benzene, toluene and the xylenes; halogenated aromatic hydrocarbons such as chlorobenzene and orthodichlorobenzene; halogenated paraffinic hydrocarbons such as methylene chloride and carbon tetrachloride; saturated hydrocarbons such as hexane, heptane, methylcyclohexane and isooctane; and nitriles such as benzonitrile and acetonitrile.

Usual met hods may be applied for work-up and to achieve product stabilization and purification. To this end, methods such as distillation, extraction, hydrolysis and reduction may be applied. The reduction may be a hydrogen treatment using a catalyst of nickel on an alumina carrier or reduction with for example sodium borohydride. The product stabilization may aim at removal of acetals by hydrolysis and of aldehydes by reduction.

The hydroformylation in accordance with this invention yields typically a branched primary alcohol composition comprising alcohols having a carbon number in the range of from 8 to 36, of which alcohols at least a portion of the molecules is branched, the average number of branches per molecule being at least 0.7 and the branching comprising methyl and optionally ethyl branches. Preferably, the branched primary alcohol composition comprises alcohols having a carbon number in the range of from 11 to 19. Preferably at least 75% w, more preferably at least 90% w, of the branched primary alcohol composition consists of alcohols having a carbon number in the range of from 11 to 19. In practice, frequently at most 99.99% w, more frequently at most 99.9% w, of the branched primary alcohol composition consists of alcohols having a carbon number in the range of from 11 to 19. When it is intended to prepare surfactant sulfates from the branched primary alcohol composition it is preferred that the branched primary alcohol composition comprises branched primary alcohols having a carbon number in the range of from 15 to 18, in which case preferably at least 75% w, more preferably at least 90% w, of the branched primary alcohol composition consists of alcohols having a carbon number in the- range of from 15 to 18. In practice, frequently at most 99.99% w, more frequently at most 99.9% w, of the branched primary alcohol composition consists of alcohols having a carbon number in the range of from 15 to 18.

Suitably the average number of branches per alcohol molecule present in the branched primary alcohol composition is at least 0.8, and preferably at least 0.9, for example 1.0. Suitably the average number of branches is at most 2.0, preferably at most 1.5, and in particular at most 1.4. The number of methyl branches is suitably at least 20%, more suitably at least 40%, preferably at least 50% of the total number of branches. In practice the number of methyl branches is frequently at most 99%, more frequently at most 98% of the total number of branches. If present, the number of ethyl branches is suitably at least 0.1%, in particular at least 1%, more in particular at least 2% of the total number of branches. Suitably, the number of ethyl branches is at most 20%, in particular at most 15%, more in particular at most 10% of the total number of branches. The number of any branches, if present, other than methyl and ethyl branches, may be less than 10%, in particular less than 5% of the total number of branches. The number of any branches, if present, other than methyl and ethyl branches, may be more than 0.1%, typically more than 1% of the total number of branches.

The number of quaternary aliphatic carbon atoms is preferably low. For applications where biodegradability is not as critical, the number of quaternary aliphatic carbon atoms is suitably less than 2% of the carbon atoms present, more suitably less than 1%. For any application, and particularly for applications where biodegradability is important, the number of quaternary aliphatic carbon atoms preferably is 0.5% or less, most preferably less than 0.5%, and in particular less than 0.3%. In practice the number of quaternary aliphatic carbon atoms is frequently more than 0.01% of the aliphatic carbon atoms present, more frequently more than 0.05%.

The content of branched primary alcohols of the branched primary alcohol composition is typically at least 70% w, more typically at least 90% w, preferably at least 95% w, more preferably at least 99% w, in particular at least 99.9% w, relatively to the weight of the branched primary alcohol composition. In practice the content of branched primary alcohols is frequently at most 99.99% w, more frequently at most 99.95% w, relatively to the weight of the branched primary alcohol composition. The content of linear alcohols of the branched primary alcohol composition is typically at most 30% w, more typically at most 10% w, preferably at most 5% w, more preferably at most 1% w, in particular at most 0.1% w, relatively to the weight of the branched primary alcohol composition. In practice the content of linear alcohols is frequently at least 0.01% w, more frequently at least 0.05% w, relatively to the weight of the branched primary alcohol composition.

The branched alcohols may be directly sulfated, or first oxyalkylated followed by sulfation. Any technique known for sulfating alcohols may be used in this invention. For example, sulfation processes suitable for application in the present invention are known from U.S. Pat. Nos. 3,462,525, 3,428,654, 3,420,875, 3,506,580, 3,579,537 and 3,524,864, each incorporated herein by reference. Suitable sulfation procedures include sulfation by reaction with oleum, sulfur trioxide ($SO_3$), chlorosulfonic acid ($ClSO_3H$) or sulfamic acid ($NH_2SO_3H$).

When oleum is used the concentration of sulfur trioxide in sulfuric acid is typically from 1 to 30% w, preferably from 2 to 20% w, based on the weight of the oleum. Suitable amounts of sulfur trioxide are generally in the range of from 0.3 to 1.3 moles per mole of branched alcohols, preferably from 0.4 to 1.0 moles per mole of branched alcohols. The sulfation may be conducted by contacting the branched alcohols and the oleum at a temperature in the range of from 20° C. to 70° C.

A typical sulfur trioxide sulfation procedure includes contacting liquid alcohol or its ethoxylate and gaseous sulfur trioxide in the reaction zone of a falling film sulfator cooled by water at a temperature in the range of from 20° C. to 70° C. to yield the sulfuric acid ester of alcohol or its ethoxylate. The reaction is suitably carried out at atmospheric pressure, for example at a pressure in the range of from 0.8 to 1.2 bara. The sulfuric acid ester of the alcohol or its ethoxylate then exits the falling film column and is neutralized with a base, e.g., sodium or potassium hydroxide, to form the corresponding alcohol sulfate salt or the corresponding alcohol ethoxysulfate salt.

Suitable oxyalkylated alcohols may be prepared by adding to the branched alcohols an amount, for example, from 0.1 to 0.6% w, preferably from 0.1 to 0.4% w, based on the weight of the branched alcohols, of a strong base, typically an alkali metal or alkaline earth metal hydroxide such as sodium hydroxide or potassium hydroxide, which serves as a catalyst for oxyalkylation. The resulting mixture is dried, as by vapor phase removal of any water present, and an amount of alkylene oxide calculated to provide from 1 to 12 moles of alkylene oxide per mole of alcohol is then introduced. The resulting mixture may be allowed to react until the alkylene oxide is consumed. The course of the reaction may be followed by following the decrease in the reaction pressure.

Suitable alkylene oxides are for example ethylene oxide, 1,2-propylene oxide, 1,2-butylene oxide and 2,3-butylene oxide. Ethylene oxide and 1,2-propylene oxide are preferred alkylene oxides. Two or more alkylene oxides may be added as a mixture to the reaction mixture alcohol, or sequentially to make a block structure.

The oxyalkylation is typically conducted at elevated temperatures and pressures. Suitable reaction temperatures range of from 120° C. to 220° C., with the range of from 140° C. to 160° C. being preferred. A suitable reaction pressure is achieved by introducing to the reaction vessel the required amount of alkylene oxide which has a high vapor pressure at the desired reaction temperature. For consideration of process safety, the partial pressure of the alkylene oxide reactant is preferably limited, for instance, to less than 5 bara, and/or the reactant is preferably diluted with an inert gas such as nitrogen, for instance, to a vapor phase concentration of 50% or less. The reaction can, however, be safely accomplished at greater alkylene oxide concentration, greater total pressure and greater partial pressure of alkylene oxide if suitable precautions, known to the art, are taken to manage the risks of explosion. With respect to ethylene oxide, a total pressure of from 4 to 10 bara, with an ethylene oxide partial pressure of from 2 to 6 bara, is preferred, while a total pressure of from 5 to 8 bara, with an ethylene oxide partial pressure of from 2.5 to 5 bara, is more preferred. In the cases that the pressure serves as a measure of the degree of the reaction these pressure ranges relate to initial pressures. In such cases the reaction is considered to be substantially complete when the pressure no longer decreases with time.

It should be understood that the oxyalkylation procedure serves to introduce a desired average number of alkylene oxide units per mole of branched alcohol oxyalkylate. For example, treatment of branched alcohols with 3 moles of ethylene oxide per mole of branched alcohol serves to effect the ethoxylation of each alcohol molecule with an average of 3 ethylene oxide moieties per mole alcohol moiety, although a substantial proportion of alcohol moieties will become combined with more than 3 ethylene oxide moieties and an approximately equal proportion will have become combined with less than 3. In a typical ethoxylation product mixture, there may also be a minor proportion of unreacted alcohol.

The general class of surfactant sulfates which may be made in accordance with this invention may be characterized by the chemical formula $(R-O-A_x-SO_3)_nM$, wherein R represents a moiety of the branched primary alcohols according to this invention which have a carbon number in the range of from 8 to 36, in particular from 11 to 19, more in particular from 15 to 18; A represents a moiety of an alkylene oxide; x represents the average number of moieties A per moiety R and is in the range of from 0 to 15; M is a cation selected from an alkali metal ion, an alkaline earth metal ion, an ammonium ion, and mixtures thereof; and n is a number depending on the valency of the cation(s) M, such that the total electrical charge is zero. The ammonium ion may be derived from an organic amine having 1, 2 or 3 organic groups attached to the nitrogen atom. Suitable ammonium ions are derived from monoethanol amine, diethanol amine and triethanol amine. It is preferred that the ammonium ion is of the formula $NH_4^+$. In preferred embodiments M represents potassium or magnesium, as potassium ions can promote the water solubility of the (branched-alkyl) arylsulfonates and magnesium can promote their performance in soft water.

Preferred classes of surfactant sulfates comprise the alkali metal sulfates of the branched primary alcohols according to this invention which have a carbon number in the range of from 11 to 19, in particular from 15 to 18, and the alkali metal sulfates of the condensation product of the branched primary alcohols having a carbon number in the range of from 11 to 19, in particular from 15 to 18, with ethylene oxide and 1,2-propylene oxide, in which condensation product the number of ethoxy groups ranges from 3 to 12 and the ratio ethoxy groups to 1,2-propoxy groups is from 4 to 12.

The surfactants which can be made in accordance with this invention, in particular the surfactant sulfates, may be used as surfactants in a wide variety of applications, including detergent formulations such as granular laundry detergent formulations, liquid laundry detergent formulations, liquid dishwashing detergent formulations; and in miscellaneous formulations such as general purpose cleaning agents, liquid soaps, shampoos and liquid scouring agents.

The surfactant sulfates find particular use in detergent formulations, specifically laundry detergent formulations. These formulations are generally comprised of a number of components, besides the surfactant sulfates themselves: other surfactants of the ionic, nonionic, amphoteric or cationic type, builders, cobuilders, bleaching agents and their activators, foam controlling agents, enzymes, anti-greying agents, optical brighteners, and stabilizers.

The present liquid laundry detergent formulations may comprise the same components as the granular laundry detergent formulations, but they generally contain less of the inorganic builder component. Hydrotropes may be present in the liquid detergent formulations. General purpose cleaning agents may comprise other surfactarits, builders, foam control agents, hydrotropes and solubilizer alcohols.

The present formulations may contain a large amount of the builder and cobuilder components, in amounts up to 90 w %, preferably between 5 and 35 w %, based on the weight of the formulation, to intensify the cleaning action. Examples of common inorganic builders are phosphates, polyphosphates, alkali metal carbonates, silicates and sulfates. Examples of organic builders are polycarboxylates, aminocarboxylates such as ethylene diaminotetraacetates, nitrilotriacetates, hydroxycarboxylates, citrates, succinates and substituted and unsubstituted alkanedi- and polycarboxylic acids. Another type of builder, useful in granular laundry and built liquid laundry agents, includes various substantially water-insoluble materials which are capable of reducing the water hardness e.g. by ion exchange processes. In particular the complex sodium aluminosilicates, known as type A zeolites, are very useful for this purpose.

The present formulations may also contain percompounds with a bleaching action, such as perborates, percarbonates, persulfates and organic peroxy acids. Formulations containing percompounds may also contain stabilizing agents, such as magnesium silicate, sodium ethylenediaminetetraacetate or sodium salts of phosphonic acids. In addition, bleach activators may be used to increase the efficiency of the inorganic persalts at lower washing temperatures. Particularly useful for this purpose are substituted carboxylic acid amides, e.g., tetraacetylethylenediamine., substituted carboxylic acids, e.g., isononyloxybenzenesulfonate and sodium-cyanamide.

Examples of suitable hydrotropic substances are alkali metal salts of benzene, toluene and xylene sulfonic acids; alkali metal salts of formic acid, citric and succinic acid, alkali metal chlorides, urea, mono-, di-, and triethanolamine. Examples of solubilizer alcohols are ethanol, isopropanol, mono- or polyethylene glycols, monopropylene glycol and etheralcohols.

Examples of foam control agents are high molecular weight fatty acid soaps, paraffinic hydrocarbons, and silicon containing defoamers. In particular hydrophobic silica particles are efficient foam control agents in these laundry detergent formulations.

Examples of known enzymes which are effective in the laundry detergent formulations are protease, amylase and lipase. Preference is given to the enzymes which have their optimum performance at the design conditions of the washing and cleaning agent.

A large number of fluorescent whiteners are described in the literature. For the laundry washing formulations, the derivatives of diaminostilbene disulfonates and substituted distyryibiphenyl are particularly suitable.

As antigreying agents, water soluble colloids of an organic nature are preferably used. Examples are water soluble polyanionic polymers such as polymers and copolymers of acrylic and maleic acid, cellulose derivatives such as carboxymethyl cellulose methyl- and hydroxyethylcellulose.

The surfactants which can be made in accordance with this invention, in particular the surfactant sulfates, may also advantageously be used in personal care products, in enhanced oil recovery applications and for the removal of oil spillage offshore and on inland waterways, canals and lakes.

The formulations according to the invention typically comprise one or more inert components. For instance, the balance of liquid detergent formulations is typically an inert solvent or diluent, most commonly water. Powdered or granular detergent formulations typically contain quantities of inert filler or carrier materials.

As used herein, the average number of branches per molecule, further particulars of the type and position of branching and the content of quaternary aliphatic carbon atoms are as defined in U.S. Pat. No. 5,849,960 and they are determined by the methods as described in U.S. Pat. No. 5,849,960. Also the further analytical methods and the test methods are as described in U.S. Pat. No. 5,849,960. U.S. Pat. No. 5,849,960 is incorporated herein by reference.

Unless specified otherwise, the low-molecular weight organic compounds mentioned herein have typically at most 40 carbon atoms, more typically at most 20 carbon atoms, in particular at most 10 carbon atoms, more in particular at most 6 carbon atoms. Organic compounds are deemed to be compounds which comprise carbon atoms and hydrogen atoms in their molecules. The group of low-molecular weight organic compounds does not include polymers and enzymes.

As defined herein, ranges for numbers of carbon atoms (i.e. carbon number) include the numbers specified for the limits of the ranges. Number of carbon atoms as defined herein include the carbon atoms along the carbon backbones, as well as branching carbon atoms, if any.

The following example will illustrate the nature of the invention without its scope.

EXAMPLE 1 (PROPHETIC)

A Fischer Tropsch hydrocarbon mixture of linear paraffins having at least 5 carbon atoms, further comprising aminor quantity of oxygenates, is subjected to conditions of hydrocracking and hydroisomerization by contacting the hydrocarbon mixture, in the presence of hydrogen, with a palladium on silica-alumina catalyst (0.5% w Pd, 55% w $Al_2O_3$, 45% w $SiO_2$) at a temperature of 350° C. and at a pressure of 60 bara, applying a liquid hourly space velocity of 0.5 l/l/h and a hydrogen to wax feed ratio of 400 Nl/l (liquid volumes at room temperature, ANl@ refers to the gas volume at 0° C., 1 bar).

The hydrocracking/hydroisomerization product stream is fractionated by distillation and by separation over a molecular sieve zeolite 5A such that an isoparaffinic composition is obtained which consists of branched and linear paraffins having a carbon number in the range of from 14 to 17. The average number of branches is 1.9 per paraffin molecule. The number of methyl branches is 60% of the total number of branches. The number of ethyl branches is 15% of the total number of branches. The quantity of branched paraffins present in the isoparaffinic composition is more than 96% w, and the quantity of linear paraffins present in the isoparaffinic composition is less than 4% w, based on the weight of the isoparaffinic composition.

The isoparaffinic composition is subjected to conditions of dehydrogenation by contacting the isoparaffinic composition, in the presence of hydrogen, with a platinum on gamma alumina catalyst (0.5% w platinum) at a temperature of 490° C. and at a pressure of 2.5 bara, applying in the feed a hydrogen/paraffins molar ratio of 4. The residence time of the isoparaffinic composition is controlled such that the conversion is 15%.

The dehydrogenation product is fractionated by separation over a molecular sieve zeolite 5A to remove paraffins. A paraffin free olefin fraction is obtained.

The olefin fraction is hydroformylated by reacting the olefin fraction with hydrogen and carbon monoxide at a molar ratio of hydrogen to carbon monoxide of 1.7:1 in the presence of a phosphine modified cobalt catalyst at a temperature of 185° C. and at a pressure of 80 bara until completion of the reaction.

The hydroformylation reaction product is subjected to usual treatments for deactivating the hydroformylation catalyst, and stabilizing, purifying and drying the alcohol product obtained.

The alcohol product is then sulfated by a known method.

EXAMPLE 2 (PROPHETIC)

The procedure of example 1 is repeated, except that the separation over a molecular sieve is omitted, and that the quantity of branched paraffins present in the isoparaffinic composition obtained is 80% w and the quantity of linear paraffins present in the isoparaffinic composition obtained is 20% w, based on the weight of the isoparaffinic composition, and in the isoparaffinic composition obtained the average number of branches is 1.5 per paraffin molecule. In other aspects the isoparaffinic composition is as indicated in example 1.

EXAMPLE 3 (PROPHETIC)

The procedure of example 1 is repeated, except that the Fischer Tropsch hydrocarbon mixture consists essentially of a wax of linear paraffins having at least 30 carbon atoms. The isoparaffinic composition obtained is of a similar composition as specified in example 1.

EXAMPLE 4 (PROPHETIC)

The procedure of example 3 is repeated, except that the separation over a molecular sieve is omitted, the quantity of branched paraffins present in the isoparaffinic composition obtained is 90% w, the quantity of linear paraffins present in the isoparaffinic composition obtained is 10% w, based on the weight of the isoparaffinic composition, and in the isoparaffinic composition obtained the average number of branches is 1.7 per paraffin molecule. In other aspects the isoparaffinic composition is as indicated in example 1.,

EXAMPLES 5–8 (PROPHETIC)

The procedures of examples 1–4 are repeated, except that in each case the isoparaffinic composition obtained consists of branched and linear paraffins having a carbon number in the range of from 13 to 17, instead of from 14 to 17. In other aspects the isoparaffinic compositions obtained are as indicated in the respective example of examples 1–4.

EXAMPLE 9

$C_{9-24}$ paraffins produced by polymerization using methane and syn gas ($H_2$ and CO) as starting materials were separated by distillation. A sample of $C_{15}$–$C_{16}$ paraffins was dehydrogenated essentially using known dehydrogenation/olefin extraction processes, to produce $C_{15}$–$C_{16}$ branched olefin (Acandidate olefins@).

A control olefin feed, which typically has a quaternary carbon content of 0.20 or less was $C_{15}$–$C_{16}$ branched olefins obtained by isomerization of linear internal olefins (AISO olefins@). The isomerization of the control was conducted essentially as described in Example 2 of U.S. Pat. No. 5,849,960 to Singleton, et al., incorporated herein by reference. The candidate olefins and the ISO olefins had the following characteristics:

TABLE 1

| | Olefin Feed | |
|---|---|---|
| Olefin type | ISO olefins | Candidate olefins |
| Olefin, % wt | 98.3 | 62 |
| Paraffin, % wt | 1.7 | 25 |
| Aromatics, % wt | 0 | 13 |

$C_{16}$–$C_{17}$ branched alcohols were synthesized from the olefin samples by hydroformylation substantially as described in the Singleton patent. Procedures performed in parallel (same conditions and procedures) were used to convert the ISO olefins to $C_{16}$–$C_{17}$ branched alcohols (ISO alcohols, D in Table 4 below) in order to provide comparison data for the candidate sample (E in Table 4 below).

The progress of the reaction was monitored by syn gas uptake. The isolation and purification steps consisted of a vacuum flash separation to remove heavy ends and catalyst residues from the crude alcohol, a sodium borohydride ($NaBH_4$) treatment to reduce formate esters and aldehydes to alcohols, a water wash step (3 times) to remove the unreacted borohydride and decomposed borate compounds; and a vacuum fractional distillation to isolate alcohols from unreacted olefins, side product paraffins, and any residual catalyst and heavy ends. The reduction of aldehydes and formate esters during the sodium borohydride treatment was monitored by FTIR.

The candidate alcohol exhibited a branching index of 1.5 and an average carbon number of 16.1. The following results for the candidate alcohols were observed:

TABLE 2

Alcohol End Branching Analysis (C-1 refers to alcohol carbon)

| | |
|---|---|
| % no branching or branching at the C4+ position | 72.0 |
| % branching at the C3 position | 11.7 |
| % methyl branching at the C2 position | 6.7 |
| % ethyl branching at the C2 | 1.4 |
| % propyl or greater branching at the C2 position | 8.3 |
| % Overall Type of Branching | |
| C1 (methyl) | 60.7 |
| C2 (ethyl) | 7.6 |
| C3+ (propyl+) | 31.6 |

The control showed the following results:

TABLE 3

Alcohol End Branching Analysis (C-1 refers to alcohol carbon)

| | |
|---|---|
| % no branching or branching at the C4+ | 63.6 |
| % branching at the C3 | 21.8 |
| % methyl branching at the C2 | 4.8 |
| % ethyl branching at the C2 | 1.3 |
| % propyl or greater branching at the C2 | 8.6 |
| % Overall Type of Branching | |
| C1 (methyl) | 79.9 |
| C2 | 10.0 |
| C3+ (propyl+) | 10.1 |

The carbon number distribution was determined using the Nitric Oxide Townsend Discharge Chemical Ionization Gas Chromatography/Mass Spectrometry method described in I. Dzidic, et al, Analytical Chemistry, Vol. 64, pp. 2227–2232 (1992). The results were as shown in the following Table:

TABLE 4

Carbon Number Distribution and Branching by CI/GC/MS

| | D (ISO alcohols) | | | E (Candidate alcohols) | | |
|---|---|---|---|---|---|---|
| | % Br alcohol | % Ln alcohol | CND | % Br alcohol | % Ln alcohol | CND |
| C14 | 0.1 | 0.0 | 0.1 | 0.0 | 0.0 | 0.0 |
| C15 | 0.7 | 0.4 | 1.1 | 0.7 | 3.0 | 3.7 |
| C16 | 26.5 | 1.0 | 27.5 | 33.9 | 14.7 | 48.6 |
| C17 | 66.7 | 0.9 | 67.5 | 38.5 | 0.8 | 39.3 |
| C18 | 3.4 | 0.0 | 3.4 | 7.8 | 0.0 | 7.8 |
| C19 | 0.4 | 0.0 | 0.4 | 0.5 | 0.0 | 0.5 |
| total | 97.8 | 2.2 | 100.0 | 81.5 | 18.5 | 100.0 |

Note:
The amount of linear alcohol is calculated based on calibration of pure standard compounds. However due to lack to suitable standards for branched components, the distribution of branched alcohol is calculated assuming equal response for all components. The resulting distribution may be close but not totally accurate.

The AAlcohol End Branching Analysis (C-1 refers to alcohol carbon)@ box describes branching in the molecule as it pertains to the location of such branches relative to the alcohol end of the molecule. When branching is present next door to the alcohol carbon (C2 carbon), the NMR is able to actually differentiate between, methyl, ethyl and propyl or longer branch types. When branching is on the carbon two away from the alcohol carbon (C3), NMR can only tell that there is a branch but can=t tell if it is a methyl, an ethyl or a propyl or longer. By the time you are three bonds away from the alcohol carbon, the NMR can=t tell if there is any kind of branching. So, the entry A%no branching or branching at the C4+ position@ coadds linear molecules as well as molecules that have branching 3+ bonds away from the alcohol carbon.

The A%Overall Type of Branching@ box gives the amounts of C1 (methyl), C2 (ethyl) and C3+ (propyl or longer) branches in the molecule irrespective of where these branches might occur relative to the alcohol end. NMR analysis of the candidate sample showed a quaternary carbon content below 0.5%. Molecules containing quaternary carbons are known to be difficult to biodegrade. Hence, a quaternary carbon content below 0.5% renders these materials very useful and quicker to biodegrade.

The Co-hydroformylation rate was calculated from the syn gas uptake using the first hour of data. Several fractions were collected during the distillation and analysed by GC-FID and FT-IR. The last two fractions of candidate alcohol (E) collected during the distillation solidified at room temperature, reference (D) sample remained in the liquid state.

EXAMPLE 10

Using the procedures described in Example 9, the quaternary carbon content of alcohol molecules found in a competitive product were measured. The competitive product was a highly methyl branched alcohol prepared by oligomerization of propylene followed by hydroformylation, which converted the olefin into a highly methyl branched alcohol. The quaternary carbon content was approximately 0.6. U.S. Pat. No. 5,112,519 describes this product as "a highly methyl branched tridecyl alcohol known for its use in lubricants and detergent formulations which does not require rapid biodegradation."

EXAMPLE 11

Sulfates of D and E from Example 9 were prepared by chlorosulfation and analyzed. The following were the results:

| Source | % AM | UOM | H2O | Sulfate | Total |
|---|---|---|---|---|---|
| D (Ex. 9) | 28.8 | 1.4 | 65.6 | 0.82 | 96.6 |
| E (Ex. 9) | 30.9 | 1.3 | 62.8 | 0.73 | 95.7 |

AM = Active Matter
UOM = Unreacted Organic Matter

It is apparent that certain features of the invention, which are for clarity described in the context of separate embodiments, may also be provides in combination in a single embodiment. Conversely, features of the invention which are described in the context of a single embodiment may also be provided separately or in any suitable sub-combination.

What is claimed is:

1. A process for preparing branched alcohol sulfates, comprising:
   converting branched olefins into said branched alcohol sulfates, said branched olefins having been obtained by a process comprising;
   subjecting a paraffinic wax to first conditions effective to hydrocrack and hydroisomerize said paraffinic wax and to produce an isoparaffinic composition comprising 0.5% or less quaternary aliphatic carbon atoms, said isoparaffinic composition comprising paraffins having a carbon number of from about 7 to about 35, at least a portion of said paraffins being branched paraffins comprising an average number of branches per paraffin molecule of at least 0.7 calculated over the total of branched paraffins and linear paraffins present, said branches comprising a first number of methyl branches and optionally a second number of ethyl branches;

exposing said isoparaffinic composition to a dehydrogenation catalyst in an amount and under dehydrogenation conditions effective to dehydrogenate said isoparaffinic composition and to produce a branched olefin composition comprising 0.5% or less quaternary aliphatic carbon atoms.

2. The process of claim 1 further comprising converting said branched olefins into branched alcohols and converting said branched alcohols into said branched alcohol sulfates.

3. The process of claim 2 wherein said converting said branched olefins into branched alcohols comprises reacting said branched olefins with carbon monoxide and hydrogen in the presence of a hydroformylation catalyst.

4. The process of claim 2 wherein said converting said branched alcohols into said branched alcohol sulfates comprises contacting said branched alcohols with a sulfating reactant under sulfating conditions effective to convert said branched alcohols to said branched alcohol sulfates.

5. The process of claim 4 wherein said sulfating reactant is selected from the group consisting of oleum, sulfur trioxide ($SO_3$), chlorosulfonic acid ($ClSO_3H$), sulfamic acid ($NH_2SO_3H$), and combinations thereof.

6. The process of claim 4 wherein said sulfating reactant is oleum.

7. The process of claim 4 wherein said sulfating reactant comprises from about 1 to about 30% w sulfur trioxide in sulfuric acid.

8. The process of claim 7 wherein said sulfur trioxide is present at from about 0.3 to about 1.3 moles per mole of branched alcohols.

9. The process of claim 7 wherein said sulfur trioxide is present at from about 0.4 to about 1.0 moles per mole of branched alcohols.

10. The process of claim 4 wherein said sulfating conditions comprise a temperature of from about 20° C. to about 70° C.

11. The process of claim 4 wherein said sulfating reactant is sulfur trioxide; and said converting said branched alcohols into said branched alcohol sulfates comprises contacting contacting said branched alcohol or an ethoxylate thereof with gaseous sulfur trioxide in a reaction zone of a falling film sulfator at a temperature of from about 20° C. to about 70° C. and at a pressure of from about 0.8 to about 1.2 bara to yield a sulfuric acid ester of said alcohol or said ethoxylate thereof.

12. The process of claim 11 further comprising neutralizing said sulfuric acid ester with a base to form sulfate salts of said sulfuric acid ester.

* * * * *